(12) United States Patent
Shi et al.

(10) Patent No.: US 9,388,184 B2
(45) Date of Patent: Jul. 12, 2016

(54) INTERMEDIATE OF ERTAPENEM, A COMPOSITION COMPRISING THE SAME AND PREPARATION METHODS THEREOF

(75) Inventors: Ying Shi, Hebei (CN); Kun Li, Hebei (CN); Zan Xie, Hebei (CN); Xuebin Zhao, Hebei (CN); Jian Lv, Hebei (CN); Xiuqin Yu, Hebei (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 455 days.

(21) Appl. No.: 13/266,947

(22) PCT Filed: Apr. 30, 2010

(86) PCT No.: PCT/CN2010/000607
§ 371 (c)(1),
(2), (4) Date: Oct. 28, 2011

(87) PCT Pub. No.: WO2010/124531
PCT Pub. Date: Nov. 4, 2010

(65) Prior Publication Data
US 2012/0095209 A1    Apr. 19, 2012

(30) Foreign Application Priority Data

Apr. 30, 2009 (CN) .......................... 2009 1 0136995

(51) Int. Cl.
*C07D 477/20* (2006.01)

(52) U.S. Cl.
CPC ............... *C07D 477/20* (2013.01); *Y02P 20/55* (2015.11)

(58) Field of Classification Search
CPC .. C07D 477/24; C07D 477/16; C07D 477/20; C07D 477/02
USPC ....................................................... 540/350
See application file for complete search history.

(56) References Cited

U.S. PATENT DOCUMENTS

| 5,478,820 | A | 12/1995 | Betts et al. |
| 5,872,250 | A | 2/1999 | Williams et al. |
| 6,504,027 | B1 | 1/2003 | Williams et al. |
| 2009/0264643 | A1* | 10/2009 | Surulichamy et al. ........ 540/350 |

FOREIGN PATENT DOCUMENTS

| CN | 101362760 A | 2/2009 |
| JP | 2005508321 A | 3/2005 |
| WO | 98/02436 A1 | 1/1998 |
| WO | 9802439 | 1/1998 |
| WO | 02/057266 A1 | 7/2002 |
| WO | 03/026572 A2 | 4/2003 |
| WO | 2008/062279 A2 | 5/2008 |

OTHER PUBLICATIONS

"Tilde." Merriam-Webster.com. Merriam-Webster, n.d. Web. Feb. 26, 2014. <http://www.merriam-webster.com/dictionary/tilde>.*
Extended European Search Report for Application No./Patent No. 10769220.4-1451/2426131, dated Oct. 7, 2013.
Curt Wentrup, Hans-Wilhelm Winter, A Stereocontrolled Synthesis of (+) – thienamycin, Department of Chemistry, University of Marburg, Lahnberge, West Germany, Mar. 24, 1980, J. Am. Chem. Soc., pp. 6161-6163.
International Search Report for International application No. PCT/CN2010/000607 mailing date of Aug. 19, 2010 with English Translation.
Karel M. J. Brands et al., "Efficient One-Pot Synthesis of the 2-Aminocarbonylpyrrolidin-4-ylthio-Cotaining Side Chain of the New Broad-Spectrum Carbapenem Antibiotic Ertapenem", Department of Process Research,, Merck Research Laboratories, New Jersey and Department of Process Research, Hertfordshire U.K., Dec. 21, 2001, J. Org. Chem. 2002 vol. 67., pp. 4771-4776.
Japanese Office Action dated Jun. 24, 2014 for Patent Application No. 2012-507577, Dispatch No. 344947, with English translation.

* cited by examiner

*Primary Examiner* — Golam M M Shameem
*Assistant Examiner* — Laura Daniel
(74) *Attorney, Agent, or Firm* — Cantor Colburn LLP

(57) ABSTRACT

Intermediates of Ertapenem of formula 2a wherein Np represents (I) or (II), and $P_1$ and $P_2$ represent carboxyl protecting groups, and their preparation methods. Compound 2a prepared by the present methods in solid form is amorphous. The present invention also relates to a composition comprising at least 95% of the intermediate of Ertapenem of formula 2a.

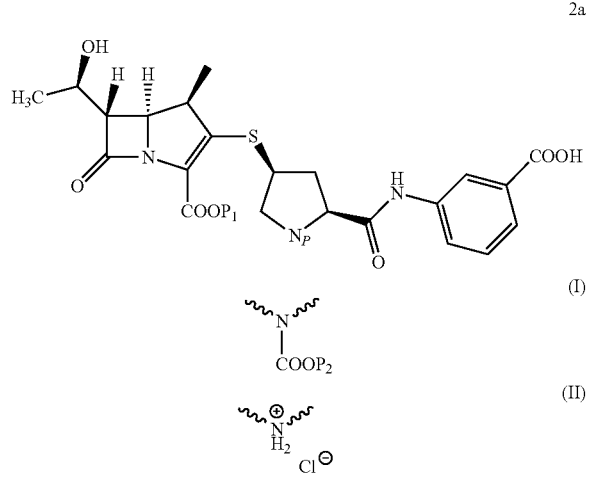

22 Claims, 1 Drawing Sheet

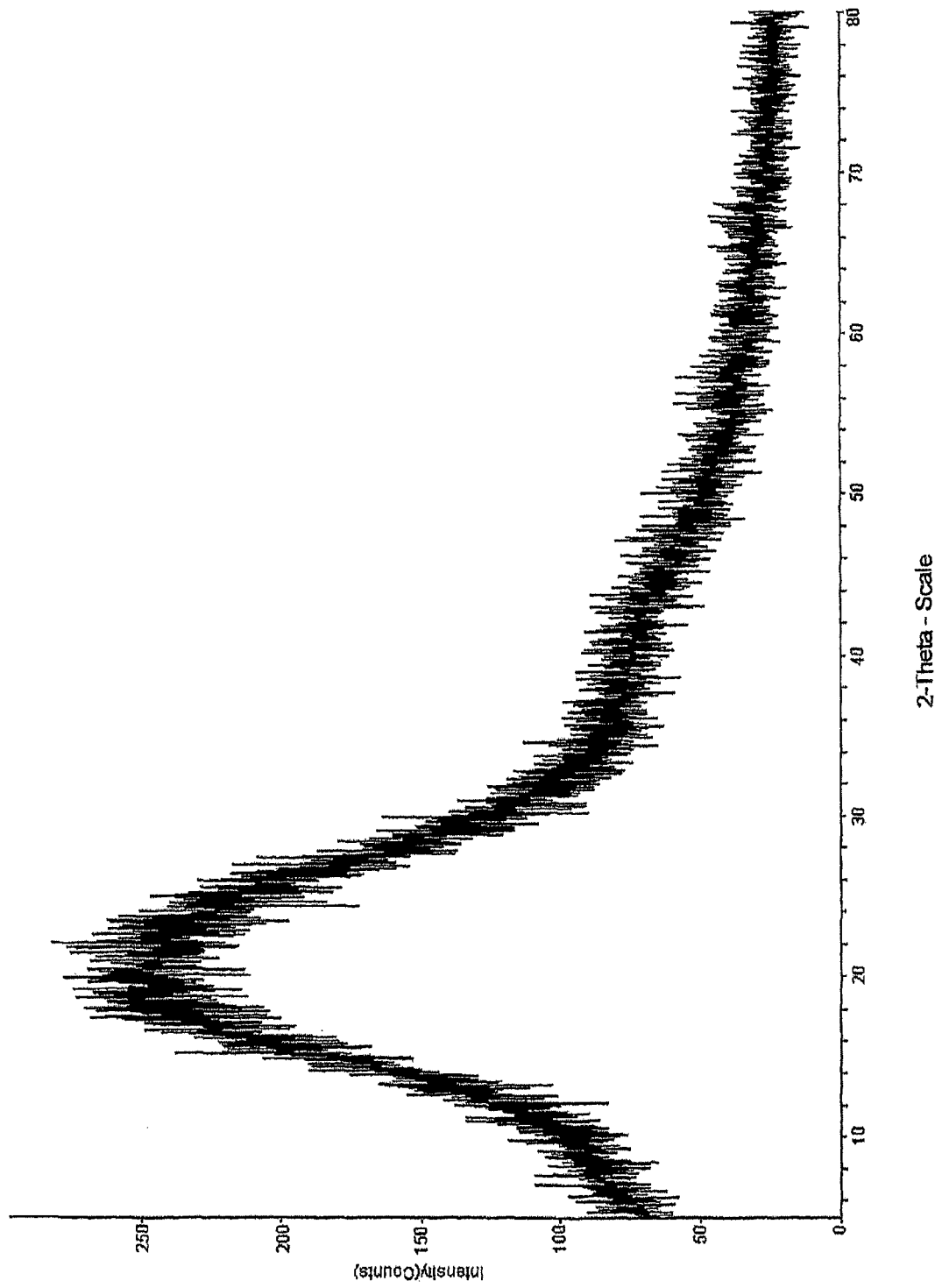

INTERMEDIATE OF ERTAPENEM, A COMPOSITION COMPRISING THE SAME AND PREPARATION METHODS THEREOF

FIELD OF THE INVENTION

The present invention relates to an intermediate of Ertapenem, and a composition comprising the same and preparation methods thereof.

BACKGROUND OF THE INVENTION

Ertapenem of formula (1) has chemical name (4R,5R,6S)-3-[(3S,5S)-5-[(3-carboxyphenyl)amino]formyl]-pyrrolidine-3-yl]thio-6-[(1R)-1-hydroxyethy]-4-methyl-7-oxo-1-azabicyclo[3.2.0]hept-2-ene-2-carboxylate, which is a new carbapenem antibiotic joint developed by Merck and Astrazeneca, and has good antibacterial activity against gram-positive bacteria and gram-negative bacterium.

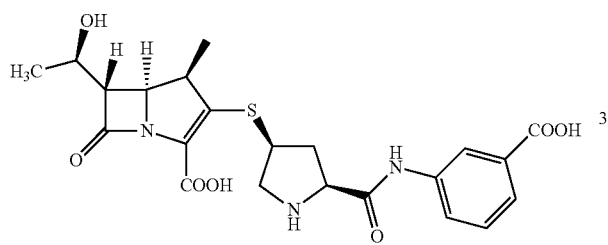

1

Ertapenem is obtained by deprotection of the intermediate of Ertapenem of formula (2).

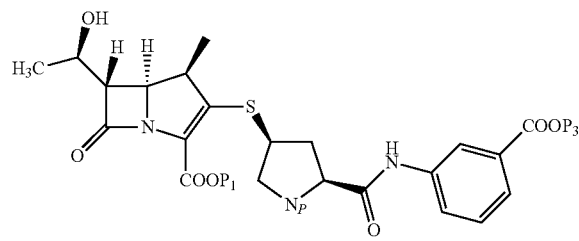

2

Np represents

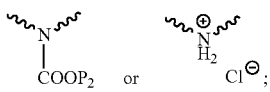

$P_1$ and $P_2$ represent carboxyl protecting groups; and $P_3$ represents carboxyl protecting groups, H or Na.

Compound 2 is typically prepared by condensing the carbapenem parent nucleus 3 with the side chain of Ertapenem 4 in the presence of base. The synthesis route is shown in Scheme 1:

Scheme 1

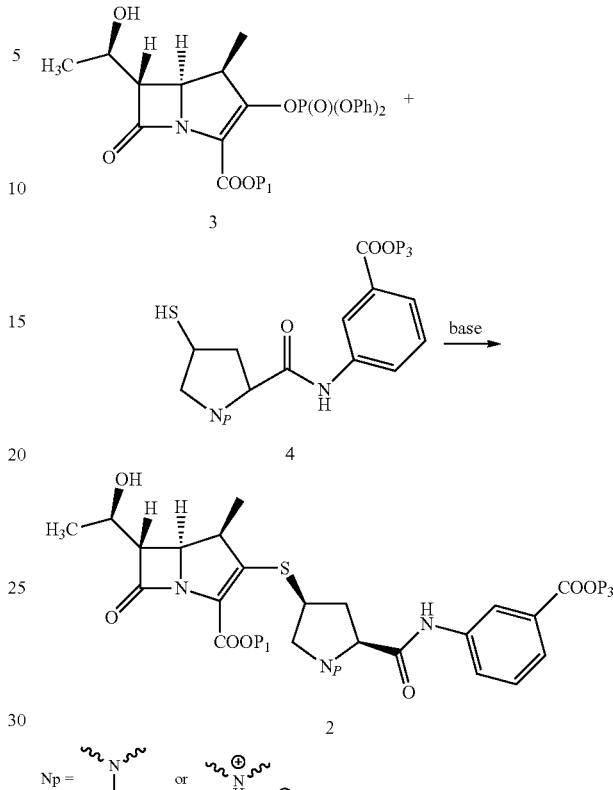

$Np = $ 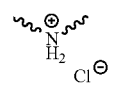

U.S. Pat. No. 5,478,820A discloses compound 2, wherein $P_1$, $P_2$ and $P_3$ are all allyl, or compound 2 wherein $P_1$ and $P_2$ are p-nitrobenzyl (referred to as PNB hereinafter) and $P_3$ is allyl, and their preparation methods.

U.S. Pat. No. 6,504,027 B1 provides a one-pot-process for producing Ertapenem sodium, which comprises condensing the carbapenem parent nucleus 3 ($P_1$ is PNB) with the side chain of Ertapenem 4 (Np is

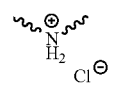

and $P_3$ is H) and deprotection by hydrogenolysis. WO 02/057266 and WO 03/026572 reported similar processes.

WO 98/02439 provides a process for producing compound 2 wherein $P_1$ and $P_2$ are both PNB and $P_3$ is H, which comprises condensing the carbapenem parent nucleus 3 ($P_1$ is PNB) with the side chain of Ertapenem 4 ($P_2$ is PNB, and $P_3$ is H) in the presence of base such as diisopropylamine with a conversion rate greater than 98%. But the aftertreatment and products obtained were not reported therein.

WO 2008/062279 provides a process for producing compound 2 wherein $P_1$ and $P_2$ are both PNB and $P_3$ is H or Na⁺. For the aftertreatment of compound 2 with $P_3$ being H, the reaction mixture was poured into buffer solution (pH=7) or water, or a mixture of buffer solution (pH=7) (or water) with ethyl acetate, and compound 2 was obtained after subsequent treatment. For the former situation, it is readily to bring about adhesion of the product and result in difficulties in aftertreatment and a poor purity (below 90%) of the product; for the latter situation, the product can not be obtained in form of solid and the process went against environmental protection due to the use of organic solvent. This application doesn't provide the physicochemical properties of the product, nor perform structure identification of the product. This application also reports a process for producing compound 2 with $P_3$ being $Na^+$ and amorphous form thereof. The introduction of sodium source results in increase of total amount of inorganic salts in subsequent reactions and thus the aftertreatment is not readily to be performed, which goes against the crystallization of product.

Consequently, there is no report on the physicochemical properties of compound 2 with $P_3$ being H in prior art, and compound 2 with $P_3$ being H can not be obtained in a high purity by the prior art. In other words, using the prior art, compound 2 with $P_3$ being H can not be obtained thereby structure identification and physicochemical properties measurement can be performed.

SUMMARY OF THE INVENTION

In the studies on Ertapenem, it is surprising that the inventors obtained an intermediate of Ertapenem of formula 2a in amorphous form, which has a high purity and good storage stability, and the preparation method used is easy and good for industrialization.

Accordingly, in one aspect, the present invention provides an intermediate of Ertapenem of formula 2a, preferably, an intermediate of Ertapenem of formula 2a in amorphous form:

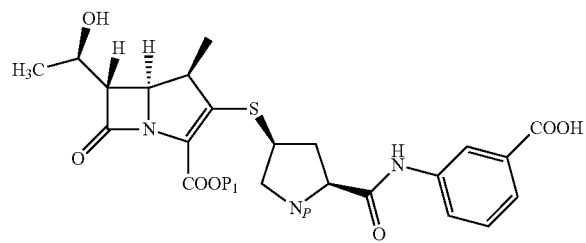

2a wherein Np represents

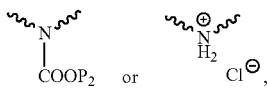

$P_1$ and $P_2$ represent carboxyl protecting groups.

DETAILED DESCRIPTION OF THE INVENTION

The carboxyl protecting group is selected from the group consisting of allyl or substituted allyl; benzyl or substituted benzyl; substituted ethyl; substituted silyl; methyl substituted by an aromatic ring; phenyl or substituted phenyl; acetonyl; t-butyl and other suitable carboxyl protecting group known by the skilled in the art.

Preferably, substituted allyl is 2-chloro allyl.
Preferably, substituted benzyl is selected from benzyl substituted by nitro and benzyl substituted by methoxyl.
Preferably, benzyl substituted by nitro is p-nitrobenzyl.
Preferably, substituted ethyl is selected from 2,2,2-trichloroethyl, 2-bromo ethyl and 2-(trimethylsilyl)ethyl.

Preferably, methyl substituted by aromatic ring is selected from 2-menaphthyl, benzhydryl, trityl and 4-pyridyl methyl.
Preferably, substituted silyl is selected from trimethylsilyl, t-butyl-dimethylsilyl and t-butyl-diphenylsilyl.
Preferably, substituted phenyl is p-methyl phenyl.
Preferably, the intermediate of Ertapenem of formula 2a includes:

p-nitrobenzyl (4R,5R,6S)-3-[(3S,5S)-5-[(3-carboxyphenyl)carbamoyl]-N-(p-nitrobenzyloxycarbonyl-pyrrolidine-3-yl]thio-6-[(1R)-1-hydroxyethyl]-4-methyl-7-oxo-1-azabicyclo[3.2.0]hept-2-ene-2-carboxylate, p-nitrobenzyl (4R,5R,6S)-3-[(3S,5S)-5-[(3-carboxyphenyl)carbamoyl]-pyrrolidine hydrochloride-3-yl]thio-6-[(1R)-1-hydroxyethyl]-4-methyl-7-oxo-1-azabicyclo[3.2.0]hept-2-ene-2-carboxylate, o-nitrobenzyl (4R,5R,6S)-3-[(3S,5S)-5-[(3-carboxyphenyl)carbamoyl]-N-(o-nitrobenzyloxy)carbonyl-pyrrolidine-3-yl]thio-6-[(1R)-1-hydroxyethyl]-4-methyl-7-oxo-1-azabicyclo[3.2.0]hept-2-ene-2-carboxylate, p-methoxybenzyl (4R,5R,6S)-3-[(3S,5S)-5-[(3-carboxyphenyl)carbamoyl]-N-(p-methoxybenzyloxycarbonyl-pyrrolidine-3-yl]thio-6-[(1R)-1- hydroxy ethyl]-4-methyl-7-oxo-1-azabicyclo[3.2.0]hept-2-ene-2-carboxylate, allylmethyl (4R,5R,6S)-3-[(3S,5S)-5-[(3-carboxyphenyl)carbamoyl]-N-(allyloxycarbonyl-pyrrolidine-3-yl)thio-6-[(1R)-1-hydroxyethyl]-4-methyl-7-oxo-1-azabicyclo[3.2.0]hept-2-ene-2-carboxylate, 2,2,2-trichloroethyl (4R,5R,6S)-3-[(3S,5S)-5-[(3-carboxyphenyl)carbamoyl]-N-(2,2,2-trichloroethyloxycarbonyl-pyrrolidine-3-yl)thio-6-[(1R)-1-hydroxyethyl]-4-methyl-7-oxo-1-azabicyclo[3.2.0]hept-2-ene-2-carboxylate, benzhydryl (4R,5R,6S)-3-[(3S,5S)-5-[(3-carboxyphenyl)carbamoyl]-N-(benzhydryloxycarbonyl-pyrrolidine-3-yl)thio-6-[(1R)-1-hydroxyethyl]-4-methyl-7-oxo-1-azabicyclo[3.2.0]hept-2-ene-2-carboxylate, trimethylsilyl (4R,5R,6S)-3-[(3S,5S)-5-[(3-carboxyphenyl)carbamoyl]-N-(trimethylsilyloxycarbonyl-pyrrolidine-3-yl)thio-6-[(1R)-1-hydroxyethyl]-4-methyl-7-oxo-1-azabicyclo[3.2.0]hept-2-ene-2-carboxylate, t-butyl (4R,5R,6S)-3-[(3S,5S)-5-[(3-carboxyphenyl)carbamoyl]-N-(t-butyloxycarbonyl-pyrrolidine-3-yl)thio-6-[(1R)-1-hydroxyethyl]-4-methyl-7-oxo-1-azabicyclo[3.2.0]hept-2-ene-2-carboxylate, More preferably, the intermediate of Ertapenem of formula 2a includes:

p-nitrobenzyl (4R,5R,6S)-3-[(3S,5S)-5-[(3-carboxyphenyl)carbamoyl]-N-(4-nitrobenzyloxycarbonyl-pyrrolidine-3-yl]thio-6-[(1R)-1-hydroxyethyl]-4-methyl-7-oxo-1-azabicyclo[3.2.0]hept-2-ene-2-carboxylate, and p-nitrobenzyl (4R,5R,6S)-3-[(3S,5S)-5-[(3-carboxyphenyl)carbamoyl]- pyrrolidine hydrochloride-3-yl]thio-6-[(1R)-1-hydroxyethyl]-4-methyl-7-oxo-1-azabicyclo[3.2.0]hept-2-ene-2-carboxylate.

In another aspect, the present invention provides a method for preparing intermediate of Ertapenem of formula 2a, particularly intermediate of Ertapenem of formula 2a in amorphous form. The method comprises condensing the carbapenem parent nucleus of formula 3 with the side chain of Ertapenem of formula 4a, characterized in that, when the reaction is finished, the reaction mixture is poured into an aqueous acid solution to yield compound of formula 2a as a solid.

The side chain of Ertapenem of formula 4a according to the present invention has the following structure:

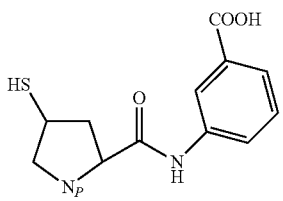

wherein Np represents

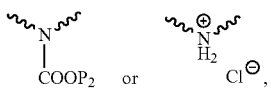

and $P_2$ represent carboxyl protecting groups.

The preparation of the carbapenem parent nucleus 3 is disclosed in, for example, *J. Am. Chem. Soc.* 1980, 102, 6161-6163, which is incorporated herein by reference.

The preparation of the side chain of Ertapenem 4a is disclosed in, for example, WO98/02439 and *J. Org. Chem.* 2002, 67, 4771-4776, which is incorporated herein by reference.

The acid is selected from an inorganic acid, an organic acid or any combination thereof, which exists in any suitable concentrations.

Preferably, the inorganic acid is selected from hydrochloride, sulfuric acid, sulfurous acid, phosphoric acid, potassium dihydrogen phosphate, sodium dihydrogen phosphate, or any combination thereof.

More preferably, the inorganic acid is selected from hydrochloride, sulfuric acid, phosphoric acid, sodium dihydrogen phosphate, or any combination thereof.

In one preferable embodiment, the inorganic acid is hydrochloride.

In one preferable embodiment, the inorganic acid is sulfuric acid.

In one preferable embodiment, the inorganic acid is phosphoric acid.

Preferably, the organic acid is selected from formic acid, acetic acid, propanoic acid, benzenesulfonic acid, p-toluenesulfonic acid, benzoic acid, oxalic acid, chloroacetic acid, trichloroacetic acid, trifluroacetic acid, or any combination thereof.

More preferably, the organic acid is selected from acetic acid, p-toluenesulfonic acid, or any combination thereof.

The pH value of the aqueous acid solution is 2~6.

Preferably, the pH value of the aqueous acid solution is 2~5.

More preferably, the pH value of the aqueous acid solution is 2.5~4.5.

Further preferably, the pH value of the aqueous acid solution is 2.5~4.

Most preferably, the pH value of the aqueous acid solution is pH 3~4.

In a further aspect, the present invention provides a composition, which comprising at least 95%, at least 96%, at least 97%, at least 98%, or at least 99% of the intermediate of Ertapenem of formula 2a, preferably, intermediate of Ertapenem of formula 2a in amorphous form, and the impurity as banlance. The impurity includes the unreacted side chain of Ertapenem of formula 4a, raw material and degradation products etc.

For the method according to the present invention, in the aftertreatment, the solvent used is water, such that organic solvent is avoid and thus the method is economic and green; the product is obtained in the form of free acid, thereby reducing the introduction of inorganic salts and thus is good for treatment of the consequent reaction; the product is in amorphous form, and the solid has high purity and is free flowable and readily for storage, and is good for treatment of the subsequent deprotection reaction.

BRIEF DESCRIPTION OF THE DRAWINGS

FIG. 1 is powder X-ray diffraction pattern of the compound 2a obtained in Example 1 of the present invention.

SPECIFIC MODES FOR CARRYING OUT THE INVENTION

The invention will be further described in combination with examples below, which however do not limit the present invention.

Instruments and Test Conditions:
  1. Powder X-ray Analysis
  Instrument: Rigaku D/MAX 2550 X-Ray diffractometer
  Scan conditions: from 5° to 80°/step length 0.02°/time spent 0.12 sec, Cu(40KV, 150 mA), I(max) 282 (peak intensity for the strongest peak I=282)(counts per sec).
  2. HPCL Analysis
  Instrument: Agilent 1100 Series,
  Column: Gemini $C_{18}$ (5μ, 250×4.6 mm)
  Test conditions: wavelength: 230 nm; mobile phase: 0.05% phosphate aqueous solution/acetonitrile=40:60 (v/v).
  3. H-NMR Analysis
  Instrument: BRUKER AVANCE II 500 MHz NMR Analyzer
  Solvent: DMSO-$d_6$
  4. MS Analysis
  Instrument: Applied Biosystems API4000 LC-MS,
  Test conditions: Positive ion ALLSCAN MODE (ESI ion source), MW range: 100-1500 amu, curtain gas (CUR): 25 L/min, shealth gas (Gs1): 35 L/min, aux gas (Gs2): 45 L/min, Ion Source (IS) voltage: 5000V, ion source temperature: 500° C., Declustering Potential (DP): 40V, and ColliSion Cell Entrance Potential (EP): 10V.
  Mobile phase: 2 mM ammonium acetate aqueous solution containing 0.5% of formic acid: methanol (50:50, V/V).

Unless indicated specifically, the above tests were performed according to the recommended program of manufacturer.

EXAMPLE 1

Preparation of Compound 2a Wherein Np Repesents

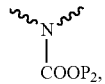

and $P_1$ and $P_2$ are Both PNB 36.0 g (0.0605 mmol) of carbapenem parent nucleus 3 ($P_1$ is PNB) was dissolved in 300 ml DMF, then 26.7 g (0.0599 mol) of the side chain of Ertapenem 4a ($P_2$ is PNB) was added. To the reaction mixture, 9.4 g (0.0727 mol) of N,N-diisopropylethylamine was added slowly at −35□. The reaction was performed under stirring. Upon completion of reaction, the reaction mixture was poured into aqueous HCl solution (pH=4), filtered, 46.6 g of solid was obtained as white or off-white powder. Purity: 98.2% (by HPLC). Yield: 98.5%. The obtained solid was analyzed by powder x-ray diffraction and the results showed the solid was in amorphous form. FIG. 1 is powder X-ray diffraction pattern of the product. H-NMR (DMSO-$d_6$): δ1.18 (d, 3H); 1.20 (d, 3H); 1.95 (m, 1H); 2.81 (m, 1H); 3.18-3.47 (m, 3H); 3.60-4.50 (m, 6H); 5.04-5.44 (m, 5H); 7.30-8.30 (m, 12H); 10.27 (d, 1H) ○ MS: 788.9 (M−1), 812.7 (M+Na).

EXAMPLE 2

Preparation of Compound 2a Wherein Np Represents

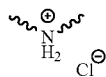

Using the preparation method of Example 1, except that carbapenem parent nucleus of formula 3 ($P_1$ represents PNB) and the side chain of Ertapenem 4a (Np represents

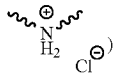

were used as the reactants. 38.4 g of solid as white or off-white powder was obtained. Purity: 98.0% (by HPLC). Yield: 98.3%. The obtained solid was analyzed by powder x-ray diffraction and the results showed the solid was in amorphous form.

MS: 645.2 (M−1), 669.1 (M+Na).

EXAMPLES 3~9

Preparation of Compound 2a Wherein Np Represents

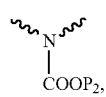

and $P_1$ and $P_2$ Represent Carboxyl Protecting Other Groups

Using the preparation method of Example 1, except that carbapenem parent nucleus 3 and the side chain of Ertapenem 4a (Np represents

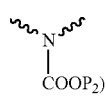

were used as the reactants, wherein $P_1$ and $P_2$ are both o-nitrobenzyl, p-methoxylbenzyl, allyl, 2,2,2-trichloroethyl, benzhydryl, trimethylsilyl and t-butyl. The results are shown in table 1:

TABLE 1

The results of Examples 3~9

| Number of example | $P_1$, $P_2$ | Yield (%) | Purity (by HPLC, %) | MS (M − 1) | Description |
|---|---|---|---|---|---|
| 3 | o-nitrobenzyl | 98.5 | 98.3 | 788.9 | solid in |
| 4 | p-methoxylbenzyl | 98.0 | 98.2 | 758.9 | amorphous |
| 5 | allyl | 97.2 | 97.9 | 598.8 | form |
| 6 | 2,2,2-trichloroethyl | 96.2 | 97.0 | 781..4 | |
| 7 | benzhydryl | 96.5 | 96.8 | 851.1 | |
| 8 | trimethylsilyl | 95.8 | 97.2 | 663.0 | |
| 9 | t-butyl | 97.5 | 97.0 | 630.9 | |

Conclusion: Using the preparation method of the present invention, condensation of the carbapenem parent nucleus 3 and the side chain of Ertapenem 4a having various protecting groups can obtain solid in amorphous form.

EXAMPLES 10~17

The Effect of Concentration of Acid on the Product

Using the preparation method of Example 1, except that the pH value of aqueous HCl solution was changed to 2, 2.5, 3, 3.5, 4.5, 5, 5.5 and 6, the results of the experiments are shown in table 2.

TABLE 2

The results of Examples 10~17

| Number of example | pH value of aqueous HCl solution | Product Weight (g) | Yield (%) | HPLC (by purity, %) | Description |
|---|---|---|---|---|---|
| 10 | 2 | 46.0 | 97.2 | 97.7 | white or |
| 11 | 2.5 | 46.4 | 98.1 | 98.0 | off-white |
| 12 | 3 | 46.5 | 98.3 | 98.4 | amorphous |
| 13 | 3.5 | 46.6 | 98.5 | 98.3 | solid |
| 14 | 4.5 | 46.4 | 98.1 | 98.1 | |
| 15 | 5 | 46.0 | 97.2 | 97.5 | |
| 16 | 5.5 | 45.7 | 96.6 | 97.0 | |
| 17 | 6 | 45.2 | 96.2 | 96.0 | |

Conclusion: The pH value of 2~5 of aqueous HCl solution is the preferred concentration of acid, since the yield and purity of the products are both over 97%. When the pH value of aqueous HCl solution is in the range of 2.5 to 4.5, the yield and purity of the products are both over 98%.

EXAMPLES 18~22

The Effect of the Kind of Acids on the Product

Using the preparation method of Example 1, except that sulfuric acid, phosphoric acid, sodium dihydrogen phosphate, acetic acid and p-toluenesulfonic acid were used instead of hydrochloride, the results were showed in table3.

TABLE 3

The results of Examples 18~22

| Number of example | aqueous acid sotion | Product Weight (g) | Yield (%) | HPLC (by purity, %) | Description |
|---|---|---|---|---|---|
| 18 | $H_2SO_4$ | 46.3 | 97.9 | 98.2 | white or |
| 19 | $H_3PO_4$ | 46.1 | 97.5 | 98.0 | off-white |
| 20 | $NaH_2PO_4$ | 46.2 | 97.7 | 97.9 | amorphous |

TABLE 3-continued

The results of Examples 18~22

| Number of example | aqueous acid sotion | Product Weight (g) | Yield (%) | HPLC (by purity, %) | Description |
|---|---|---|---|---|---|
| 21 | acetic acid | 46.0 | 97.2 | 97.6 | solid |
| 22 | p-toluenesulfonic acid | 45.8 | 96.8 | 96.6 | |

Conclusion: Different kinds of inorganic acid and organic acid can be used in the invention, and the yield and purity of the obtained products are over 96%.

COMPARATIVE EXAMPLES

Experimental Results the Examples of Compound 2a ($P_1$ and $P_2$ are both PNB) in Related Patent WO2008062279.

Comparative Example 1

Experimental Result of Example 1 of WO2008062279

8.3 g of the side chain of Ertapenem 4a (Np represents

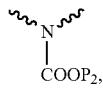

and $P_2$ is PNB) was dissolved in 30 mL DMF, to which 10 g of carbapenem parent nucleus 3 ($P_1$ is PNB) was added. To the reaction mixture, 5.4 g of diisopropylethylamine (DIPEA) was added at −30° C. and stirred. Upon completion of reaction, the reaction mixture was diluted with 60 mL of THF, and was poured into a mixture of buffer solution (pH=7) and 300 mL of ethyl acetate. The organic layer was separated, the filtrate was washed with aqueous NaCl solution and treated with activated carbon. Solvent was removed by concentration under reduced pressure at 40° C. The residue was stirred with 50 mL of ethyl acetate, and no solid was precipitated.

Comparative Example 2

Experimental Result of Example 3 of WO2008062279

8.3 g of the side chain of Ertapenem 4a (Np represents

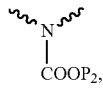

and $P_2$ is PNB) was dissolved in 30 mL DMF, to which 10 g of carbapenem parent nucleus 3 ($P_1$ is PNB) was added. To the reaction mixture, 5.4 g of diisopropylethylamine (DIPEA) was added at −30° C. and stirred. Upon completion of reaction, the reaction mixture was poured into water and stirred. The product adhered to conglobation. After filtered under reduced pressure, the solid obtained was difficult to wash. The solid was dried and determined to find the purity is 86% (by HPLC). Recrystallization was performed using one or more kinds of solvent system such as ester, ketone, halohydrocarbon, alkane, aromatic hydrocarbon, alcohol, ether, non-protonic solvent and water, and no solid was precipitated.

Conclusion: it can be known from the results of comparative examples 1 and 2, by the preparation methods disclosed in the examples 1 and 3 of WO2008062279, no solid could be obtained, or the obtained solid has a poor purity which is not suitable for storage, and can not be used for structure identification.

What is claimed is:

1. A solid composition comprising at least 95% of intermediate of Ertapenem of formula 2a in amorphous solid form:

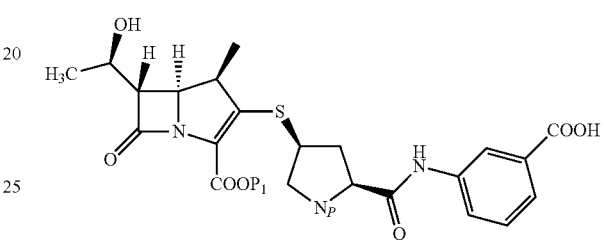

wherein Np represents

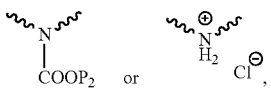

and $P_1$ and $P_2$ represent carboxyl protecting groups, together with impurity as balance.

2. The solid composition according to claim 1, wherein the carboxyl protecting group is selected from the group consisting of allyl or substituted allyl, benzyl or substituted benzyl, substituted ethyl, substituted silyl, methyl substituted by aromatic ring, and phenyl or substituted phenyl.

3. The solid composition according to claim 1, wherein Np represents

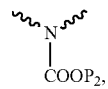

$P_1$ and $P_2$ are independently selected from the group consisting of p-nitrobenzyl, o-nitrobenzyl, p-methoxylbenzyl, allyl, 2,2,2-trichloroethyl, benzhydryl, trimethylsilyl, and t-butyl.

4. The solid composition according to claim 1, wherein Np represents

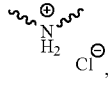

and $P_1$ represents p-nitrobenzyl, o-nitrobenzyl, p-methoxylbenzyl, allyl, 2,2,2-trichloroethyl, benzhydryl, trimethylsilyl, or t-butyl.

5. A method for preparing the solid composition according to claim 1,
comprising condensing the carbapenem parent nucleus of formula 3

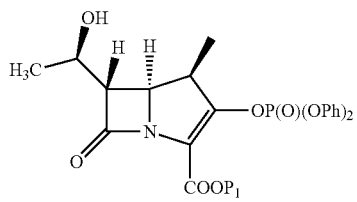

3 wherein $P_1$ represents carboxyl protecting groups, with the side chain of Ertapenem of formula 4a,

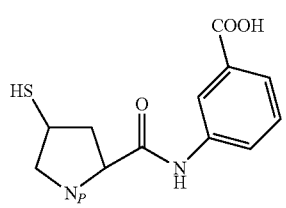

4a wherein Np represents

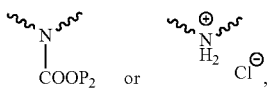

and $P_2$ represents a carboxyl protecting groups,
characterized in that, when the reaction is finished, the reaction mixture is poured into an aqueous acid solution.

6. The method according to claim 5, characterized in that, the acid is selected from an inorganic acid, an organic acid or a combination thereof.

7. The method according to claim 6, characterized in that, the acid is selected from hydrochloride, sulfuric acid, sulfurous acid, phosphoric acid, potassium dihydrogen phosphate, sodium dihydrogen phosphate, formic acid, acetic acid, propanoic acid, benzenesulfonic acid, p-toluenesulfonic acid, benzoic acid, oxalic acid, chloroacetic acid, trichloroacetic acid, trifluroacetic acid.

8. The method according to claim 6, characterized in that, the acid is selected from hydrocholoride, sulfuric acid, phosphoric acid, sodium dihydrogen phosphate, acetic acid and p-toluenesulfonic acid.

9. The method according to claim 6, characterized in that, the acid is hydrocholoride.

10. The method according to claim 6, characterized in that, the acid is sulfuric acid.

11. The method according to claim 6, characterized in that, the acid is phosphoric acid.

12. The method according to claim 6, characterized in that, the pH value of the aqueous acid solution is within the range from 2 to 6.

13. The solid composition according to claim 1, wherein the carboxyl protecting group is selected from the group consisting of 2-chloro allyl, benzyl substituted by nitro and benzyl substituted by methoxyl, 2,2,2-trichloroethyl, 2-bromo ethyl, 2-trimethylsilyl ethyl, trimethylsilyl, t-butyl-dimethylsilyl, t-butyl-diphenylsilyl, 2-naphthylmethyl, benzhydryl, trityl, 4-pyridyl methyl, p-methyl phenyl, acetonyl and t-butyl.

14. The solid composition according to claim 1, wherein Np represents

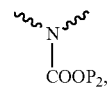

$P_1$ and $P_2$ are both p-nitrobenzyl.

15. The solid composition according to claim 1, wherein Np represents

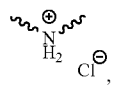

$P_1$ represents p-nitrobenzyl.

16. The method according to claim 6, characterized in that, the pH value of the aqueous acid solution is within the range from 2 to 5.

17. The method according to claim 6, characterized in that, the pH value of the aqueous acid solution is within the range from 2.5 to 4.5.

18. The method according to claim 6, characterized in that, the pH value of the aqueous acid solution is within the range from 2.5 to 4.

19. The method according to claim 6, characterized in that, the pH value of the aqueous acid solution is within the range from 3 to 4.

20. The solid composition according to claim 1, comprising at least 96% of intermediate of Ertapenem of formula 2a in amorphous solid form, together with impurity as balance.

21. The solid composition according to claim 1, comprising at least 97% of intermediate of Ertapenem of formula 2a in amorphous solid form, together with impurity as balance.

22. The solid composition according to claim 1, comprising at least 98% of intermediate of Ertapenem of formula 2a in amorphous solid form, together with impurity as balance.

* * * * *